(12) United States Patent
Mizouchi

(10) Patent No.: US 6,798,577 B2
(45) Date of Patent: Sep. 28, 2004

(54) ILLUMINATION APPARATUS WITH LIGHT SHIELDING NEAR AN EXIT PLANE OF AN OPTICAL PIPE AND PROJECTION EXPOSURE APPARATUS USING SAME

(75) Inventor: Satoru Mizouchi, Tochigi (JP)

(73) Assignee: Canon Kabushiki Kaisha (JP)

( * ) Notice: Subject to any disclaimer, the term of this patent is extended or adjusted under 35 U.S.C. 154(b) by 0 days.

(21) Appl. No.: 10/656,660

(22) Filed: Sep. 5, 2003

(65) Prior Publication Data

US 2004/0051953 A1 Mar. 18, 2004

Related U.S. Application Data

(63) Continuation of application No. 10/053,191, filed on Jan. 15, 2002.

(30) Foreign Application Priority Data

Jan. 15, 2001 (JP) .................................. 2001-006809

(51) Int. Cl.[7] .......................... G02B 27/10; G03B 27/42
(52) U.S. Cl. ......................................... 359/619; 355/53
(58) Field of Search ..................... 355/67, 53; 359/618, 359/619; 362/268

(56) References Cited

U.S. PATENT DOCUMENTS 4,918,583 A * 4/1990 Kudo et al. .................. 366/268
5,636,003 A * 6/1997 Tanitsu et al. ................. 355/67

* cited by examiner

Primary Examiner—David N. Spector
(74) Attorney, Agent, or Firm—Morgan & Finnegan, LLP

(57) ABSTRACT

An illumination apparatus includes an inner-surface reflecting type integrator, an optical system for directing a beam from a light source to a portion of incidence of the inner-surface reflecting type integrator, an wave-front splitting type integrator, an image-forming optical system for arranging the portion of incidence of the inner-surface reflecting type integrator approximately conjugate with a portion of incidence of the wave-front splitting type integrator, and for directing a beam from the beam mixer to the wave-front splitting type integrator, and an irradiating optical system for superimposing multiple beams from the wave-front splitting type integrator on a plane to be irradiated, wherein a stop is provided at or near the portion of exit of the inner-surface reflecting type integrator.

15 Claims, 9 Drawing Sheets

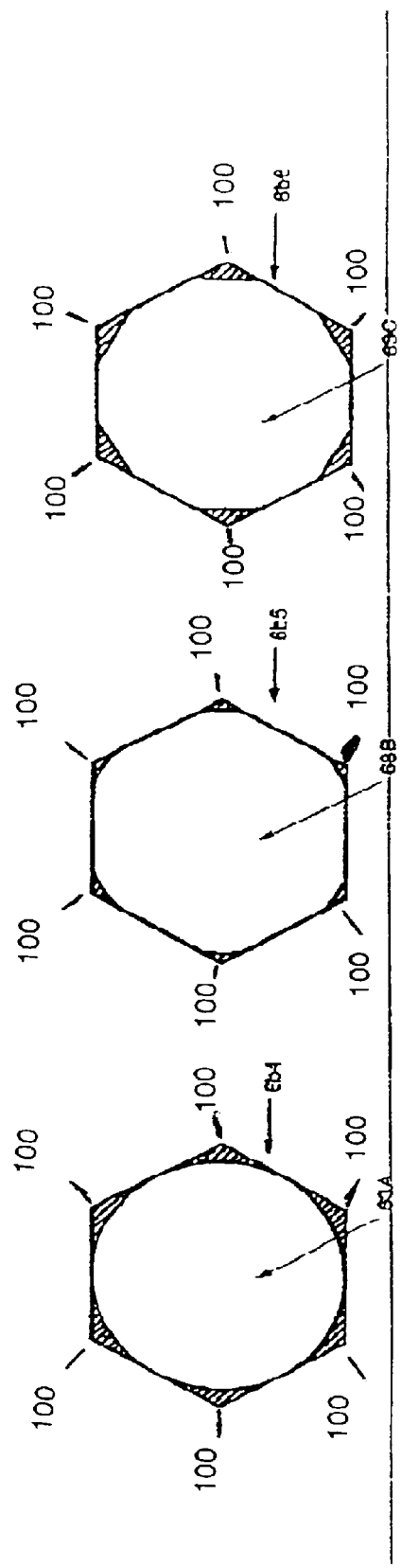

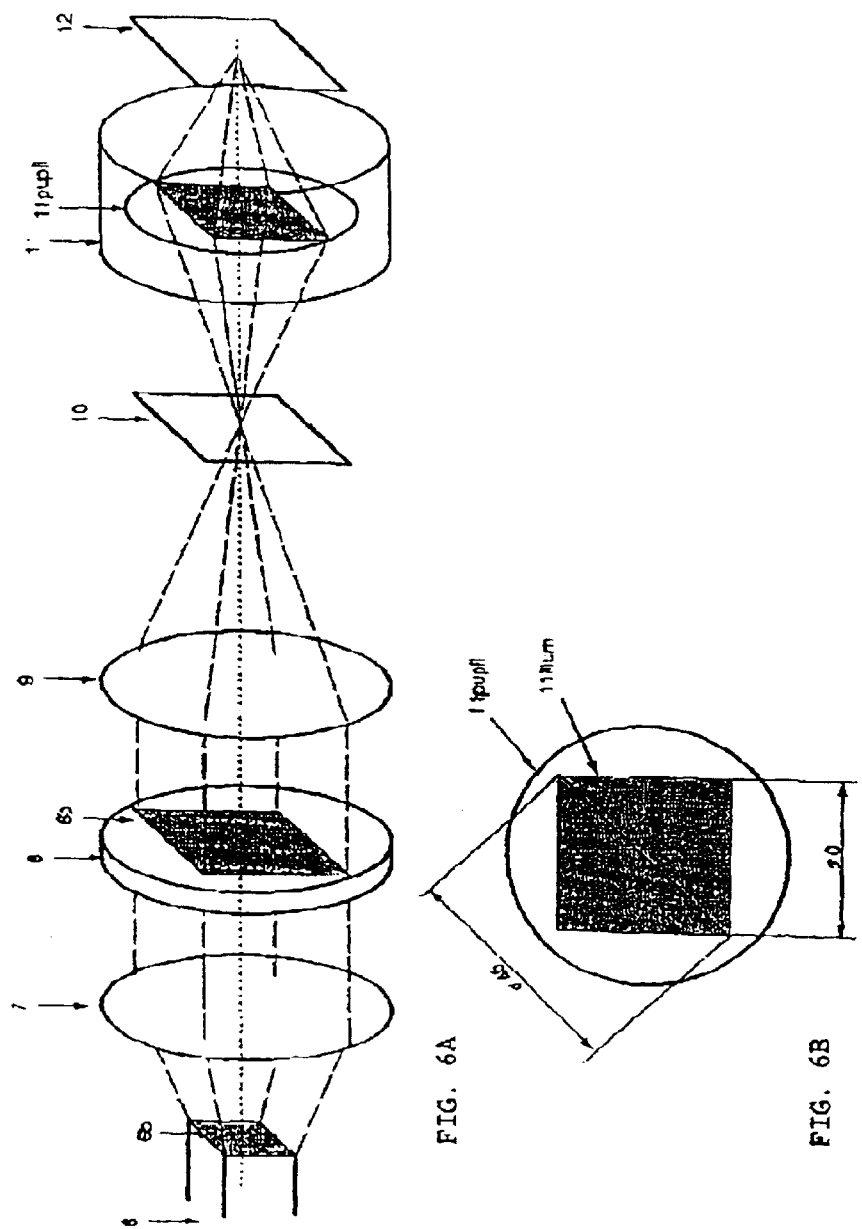

ILLUMINATION APPARATUS WITH LIGHT SHIELDING NEAR AN EXIT PLANE OF AN OPTICAL PIPE AND PROJECTION EXPOSURE APPARATUS USING SAME

This is continuation of co-pending application Ser. No. 10/053,191, filed Jan. 15, 2002.

BACKGROUND OF THE INVENTION

This invention relates to projection exposure apparatuses and device fabrication methods using these apparatuses. Specifically, the present invention is suitably applicable to a projection exposure apparatus, e.g., of a step-and-repeat or a step-and-scan type, as a kind of fabrication apparatus used in a lithography process for devices such as semiconductor devices, which properly illuminates reticle and wafer surfaces to facilitate a high resolution.

The conventional process for fabricating semiconductor chips sequentially overlays and transfers minute patterns created on multiple masks onto a wafer surface.

This operation uses an illumination apparatus in an exposure apparatus to illuminate a mask (or reticle) arranged in a position optically conjugate with the wafer, so as to project and transfer a pattern on the mask onto the wafer surface via a projection lens.

The image quality of the pattern transferred onto the wafer is primarily dependent on the performance of the illumination apparatus, for example, the uniformity of its luminous intensity distribution on the mask and wafer. For example, Japanese Laid-Open Patent Application No. 10-270312 discloses the illumination apparatus that uses an inner-surface reflecting optical integrator (or a beam mixer) and a wave-front splitting optical integrator (or a multi-beam generating means) to improve the uniformity of the luminous intensity distribution.

FIG. 5 shows a partial schematic view of a projection exposure apparatus that uses an illumination apparatus which employs inner-surface reflecting and a wave-front splitting integrators.

FIG. 5 shows a step-and-repeat or step-and-scan projection exposure apparatus used for fabricating semiconductor chips such as LSIs and VLSIs, and devices such as CCDs, magnetic sensors, and liquid crystal devices.

In FIG. 5, 1 denotes a laser light source such as an ArF or KrF excimer laser. 2 denotes an incoherently turning optical system (a coherency decreasing means) that turns a coherent laser beam from the light source 1 into an incoherent one so that there may be no speckles on a plate 12. 3 denotes a beam shaping optical system for shaping a beam from the incoherently turning optical system 2 into a desired beam shape. 4 denotes an optical element for retaining an angle of exit, and for serving to maintain the angle of exit constant regardless of a status of an incident beam.

5 is a condensing optical system, which condenses beams from the optical element 4 and leads them to a plane of incidence 6a of the optical pipe 6 (or beam mixing means). The beam mixing means 6 uses beams from the condensing optical system 5 to create multiple virtual light sources (virtual images of the light source), and mix beams from multiple virtual light sources so as to make the luminous intensity distribution uniform on the plane of exit 6b.

7 denotes a zoom optical system (or image-forming system). This optical system 7 projects beams from the beam mixing means 6 onto a plane of incidence 8a of a fly-eye lens as the multiple beams generating means 8 under various magnifications, and enables (a coherence factor) σ to change continuously during zooming. At that time, the optical pipe 6's plane of exit 6b and the fly-eye lens 8's plane of incidence 8a are approximately conjugate with each other. In other words, the optical system 8 can form an image on the plane of exit 6b onto the plane of incidence 8a, and change the image size.

The fly-eye lens 8 forms multiple secondary light source images in the neighborhood of its plane of exit 8b.

9 denotes an irradiating means including a condenser lens and the like, which condenses a beam from each element lens in the multiple beams generating means 8, and superimposes and uniformly illuminates a plane to be irradiated 10 as a plane forming a pattern on a mask or reticle (called a "reticle" hereinafter).

11 is a projection optical system. The optical system 11 has a telecentric system at the side of its plane of exit, and demagnifies and projects the pattern on the reticle 10 onto the wafer (plate) 12.

FIG. 6(A) is a schematic view from the optical pipe 6 to the wafer 12 in the above conventional example described above, addressing σ (or the size of an illumination beam within a plane of pupil) in the projection optical system 11, where the optical pipe 6 has a square cross section.

Optical pipe 6's plane of exit 6b that includes the square cross section is transcribed to the fly-eye lens 8's plane of incidence 8a in an approximately conjugate manner through a zoom optical system 7. Since the fly-eye lens 8 is an aggregate of element lenses, the light quantity distribution on the plane of incidence 8a is transmitted on an as-is basis to the plane of exit 8b.

Therefore, for the square 6b in this case, 8b also has a square light quantity distribution.

Beams exiting from the fly-eye lens 8's plane of exit 8b pass through the condenser lens 9 and Kohler-illuminates the reticle 10. The plane of exit 8b and projection optical system 11's plane of pupil $11_{pupil}$ are in an approximately conjugate relationship.

If a distribution of illumination light in projection optical system 11's plane of pupil $11_{pupil}$ is indicated as $11_{illum}$, the illumination light distribution $11_{illum}$ also becomes a square distribution from the above relationship as shown in FIG. 6(B).

σ represents the magnitude of the illumination light in projection optical system's plane of pupil. However, in this case, a ratio between σ0 in a direction of 0° (or a vertical direction in the figure) and σ45 in a direction of 45° to the direction 0° is a ratio between a side length and a diagonal length in a square, as can be understood from FIG. 6(B). Consequently, σ45 is 1.41 times as large as σ0.

This means that open angles (NA) of a beam that illuminates one spot on the reticle 10 differs in the directions of 0° and 45°, which, in turn, means that a difference in resolving power occurs in relation to these two directions when a pattern on the reticle 10 is projected onto the wafer 12.

A σ adjustment stop having, e.g., a circular aperture, when provided before the fly-eye lens 8' plane of exit 8b would eliminate the foregoing anisotropy of σ. However, this requires so many σ adjustment stops corresponding to the number of kinds of a settings, making the continuous σ changing practically impossible.

Accordingly, it is an object of the present invention to provide an improved projection exposure apparatus having no the above σ anisotropy.

In addition, it is a supplementary object to provide a projection exposure apparatus that miniaturizes an illumination system and improves the durability, without lowering luminous intensity, and without necessarily requiring a switching mechanism for the a adjustment stop at the side of fly-eye lens's plane of exit.

BRIEF SUMMARY OF THE INVENTION

In order to achieve the foregoing object, an illumination apparatus of one aspect of the present invention includes an inner-surface reflecting type integrator, an optical system for directing a beam from a light source to a portion of incidence of the inner-surface reflecting type integrator, an wave-front splitting type integrator, an image-forming optical system for arranging the portion of incidence of the inner-surface reflecting type integrator approximately conjugate with a portion of incidence of the wave-front splitting type integrator, and for directing a beam from the beam mixer to the wave-front splitting type integrator, and an irradiating optical system for superimposing multiple beams from the wave-front splitting type integrator on a plane to be irradiated, wherein a stop is provided at or near the portion of exit of the inner-surface reflecting type integrator.

The inner-surface reflecting type integrator may reflect at least a part of incident light with an internal surface of the inner-surface reflecting optical integrator, and for forming a surface light source on or near the plane of exit of the inner-surface reflecting optical integrator. The inner-surface reflecting type integrator may be a lens array for splitting a wave front of incident light, and for forming multiple secondary light sources on or near the portion of exit of the inner-surface reflecting type integrator.

The stop may be a mechanical aperture stop. Alternatively, the stop may be made of a light shielding material applied onto the portion of exit of the inner-surface reflecting type integrator, or made of a multi-layer film vapor-deposited onto the portion of exit of the inner-surface reflecting type integrator, or made of a metallic film vapor-deposited onto the portion of exit of the inner-surface reflecting type integrator.

In the foregoing illumination apparatus, the image-forming system may be a zoom optical system.

The portion of exit of the beam mixer may have a polygonal shape, and the stop may have an aperture for correcting σ anisotropy. The stop has an approximately circular aperture. The stop has apertures having an approximately equal diameter at least in four directions of 0°, 45°, 90°, and 135°.

An illumination apparatus of another aspect of the present invention includes an inner-surface reflecting type integrator including a portion of exit with an n-gonal shape where n is a natural number, a wave-front splitting type integrator, a zoom optical system for projecting an image of the portion of exit of the inner-surface reflecting type integrator, onto a portion of incidence of the wave-front splitting type integrator, and an irradiating optical system for superimposing multiple beams from the wave-front splitting type integrator on a plane to be irradiated, wherein a stop having an approximately circular aperture is provided at or near the portion of exit of the inner-surface reflecting type integrator.

An illumination apparatus of still another aspect of the present invention includes an inner-surface reflecting type integrator including a portion of exit with a n-gonal shape where n is a natural number, a first condensing optical system for condensing a beam from a light source to a portion of incidence of the inner-surface reflecting type integrator, a wave-front splitting type integrator, a zoom optical system for projecting an image of the portion of exit of the inner-surface reflecting type integrator, onto a portion of incidence of the wave-front splitting type integrator, and a second condensing optical system for condensing a beam from an irradiating optical system for superimposing multiple beams from the wave-front splitting type integrator on a plane to be irradiated, wherein there is provided a stop having an aperture with an approximately 2n-gonal shape where n is a natural number at or near a portion of incidence of the inner-surface reflecting type integrator.

A projection exposure apparatus of still another aspect of the present invention includes any one of the above illumination apparatuses for illuminating a mask located on a plane to be illuminated, and a projection optical system for projecting a pattern on the mask onto a wafer. A device fabrication method of still another aspect of the present invention includes the steps of projecting a pattern on a mask onto a wafer by using one of the above projection exposure apparatuses, and developing the wafer to which the pattern was transferred.

BRIEF DESCRIPTION OF THE DRAWINGS

FIG. 3(A) is a view of optical pipe's plane of exit and a light shielding means of a fourth embodiment according to the present invention. FIG. 3(B) a view of optical pipe's plane of exit and a light shielding means of a fifth embodiment according to the present invention. FIG. 3(C) is a view of optical pipe's plane of exit and a light shielding means of a sixth embodiment according to the present invention.

FIG. 6 is a detailed schematic view of a conventional example.

DETAILED DESCRIPTION OF THE PREFERRED EMBODIMENTS

Figure 1:
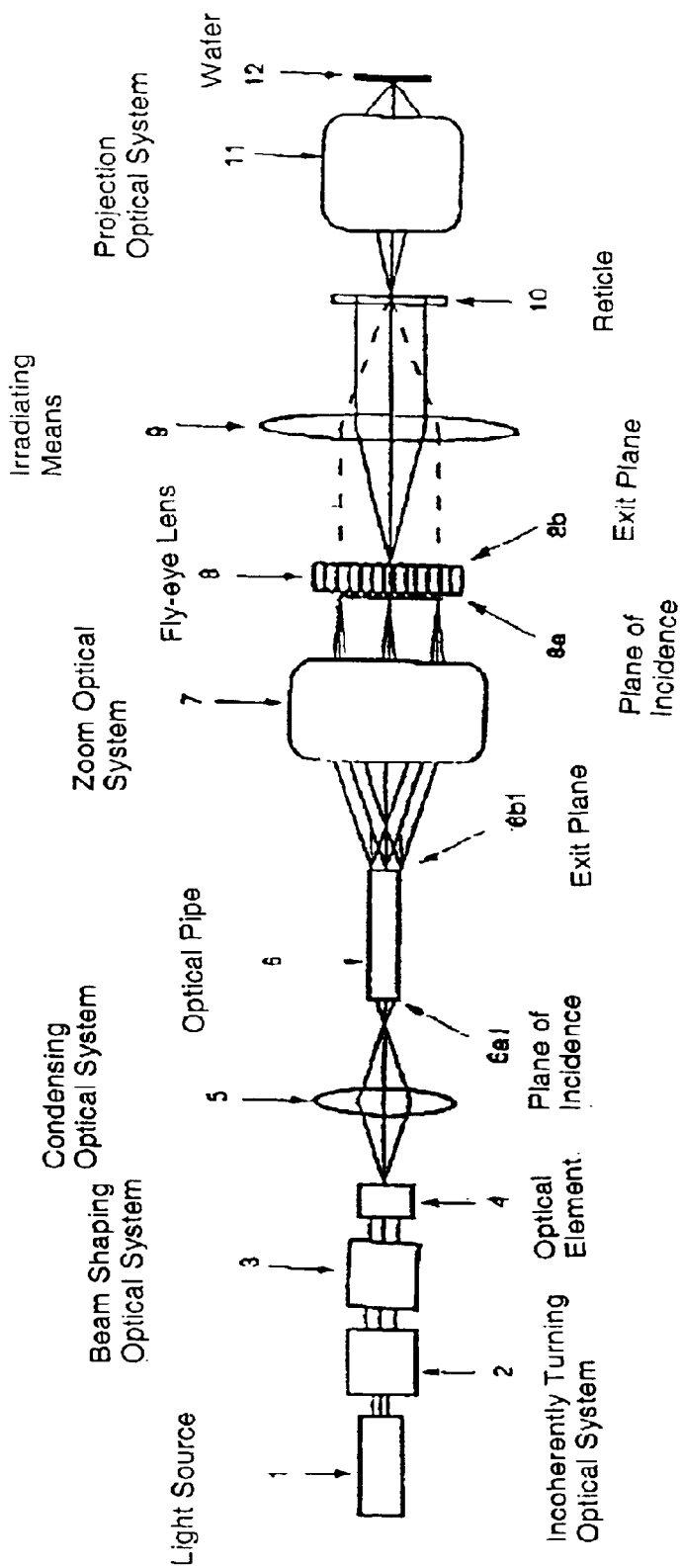
FIG. 1 is a schematic view of a first embodiment according to the present invention.

FIG. 1 shows a schematic view of main parts of a first embodiment according to the present invention.

Figure 5:
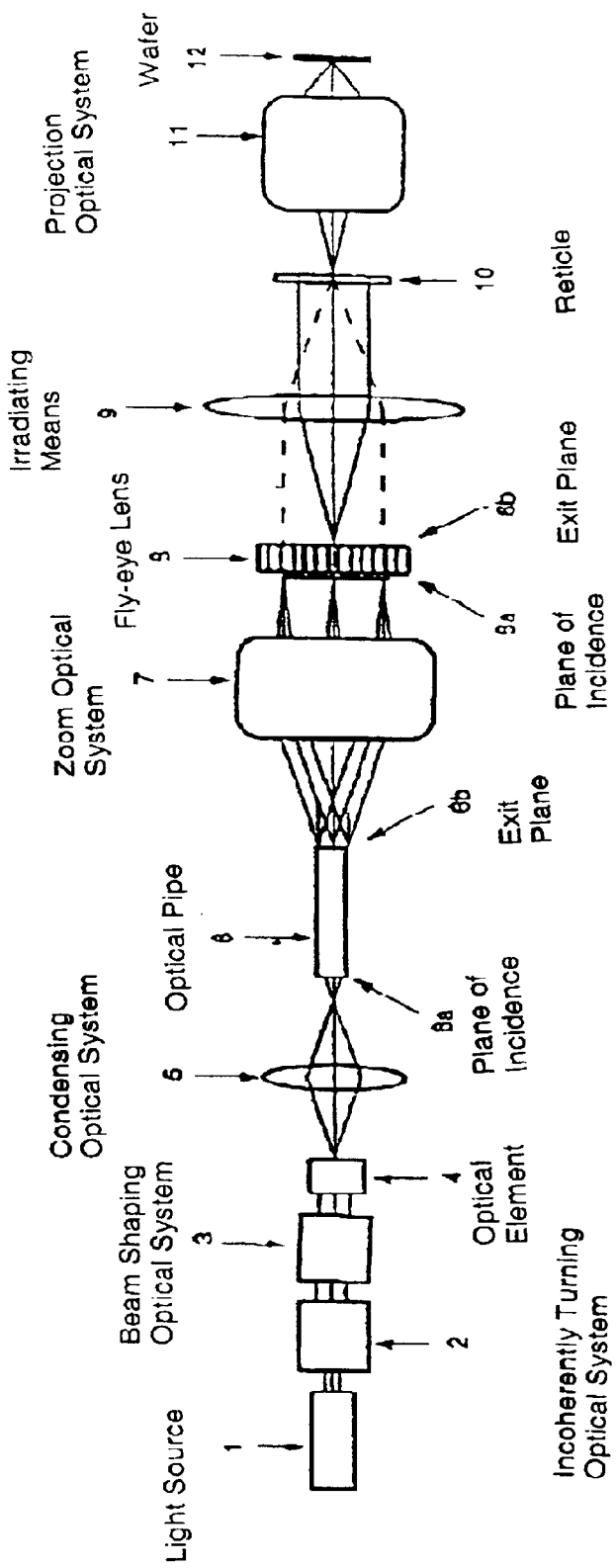
FIG. 5 is a schematic view of a conventional example.

A difference between the first embodiment and the conventional example described with reference to FIG. 5 is directed only to a difference in a plane of exit of the optical pipe 6, and therefore a description of other main parts will be omitted.

Figures 2A, 2B, 2C:
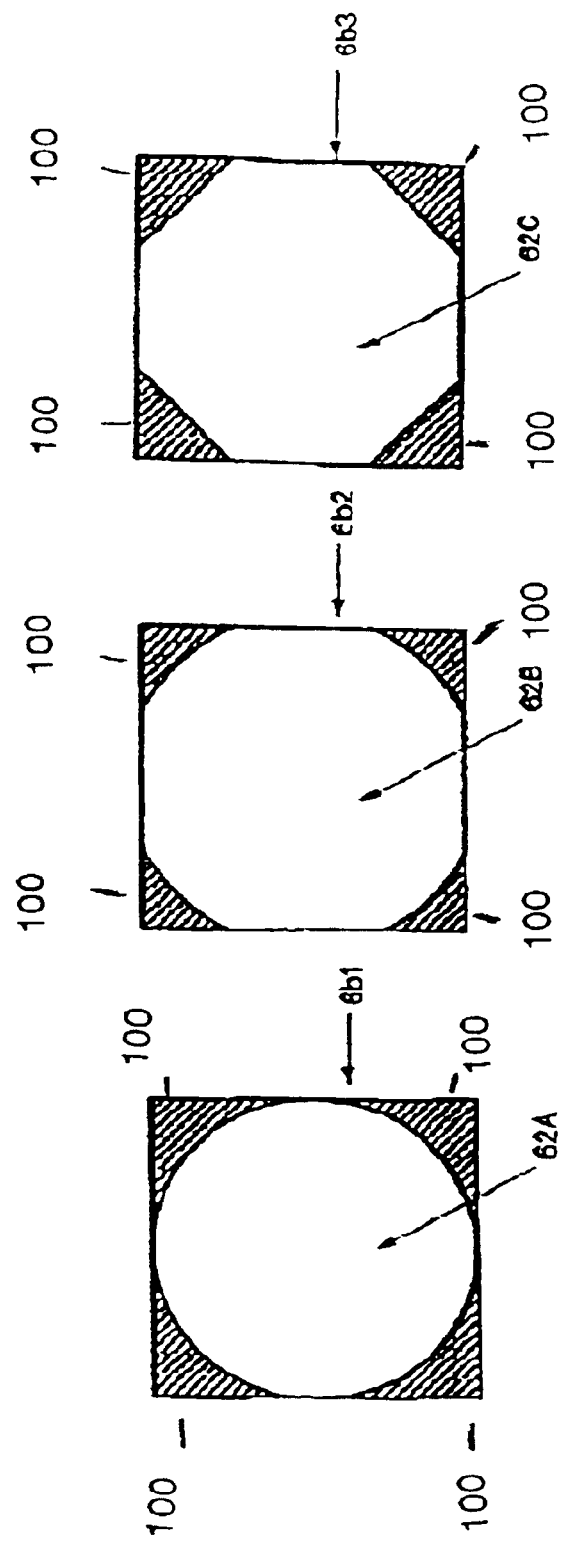
FIG. 2(A) is a view of optical pipe's plane of exit and a light shielding means of the first embodiment according to the present invention.
FIG. 2(B) is a view of optical pipe's plane of exit and a light shielding means of a second embodiment according to the present invention.
FIG. 2(C) is a view of optical pipe's plane of exit and a light shielding means of a third embodiment according to the present invention.

In the present embodiment, the optical pipe 6 has a square cross section vertical to the optical axis, and its square plane of exit 6b is shown in FIG. 2(A).

The optical pipe 6's plane of exit 6b is provided with a light shielding means 100 as indicated by slanting lines in the figure. The slanting-line area shields the light, and thus a section vertical to the optical axis of the exiting illumination light has a circular shape as denoted by 62A. Thus, a projection exposure apparatus according to the present embodiment has no conventional problem of the anisotropy of (coherence factor) σ.

Further, since the light shielding means 100 is provided near the optical pipe 6's plane of exit 6b, it is not necessarily required to provide the fly-eye lens 8's plane of exit 8b with a σ adjustment stop because when σ changes continuously, a zoom optical system projects (or forms an image through a circular aperture) a beam shaped by the light shielding means 100 such that σ may be isotropic.

The light shielding means 100 may be, e.g., a mechanical stop with a circular aperture (for example, made of a metal sheet). Alternatively, the light shielding means 100 may be made of a light shielding material applied onto the optical pipe 6's plane of exit 6b except for its circular (or aperture) area, or made of a dielectric multi-layer film or metallic film such as chromium vapor-deposited onto the optical pipe 6's plane of exit 6a except for its circular (or aperture) area.

FIG. 2(B) shows a second embodiment according to the present invention. The illumination light formed by the light shielding means according to the first embodiment has a circular section inscribed in the square of the optical pipe 6's plane of exit 6b. On the other hand, the second embodiment uses a circle slightly larger such that the section of the illumination light does not internally touch the optical pipe 6's plane of exit 6b, deforming the sectional shape 62B of the illumination light out of a circle to the extent of the permissible a anisotropy.

Since the area of the aperture is larger than that of the first embodiment, the optical utilization efficiency is improved.

FIG. 2(C) shows a third embodiment. This embodiment makes a regular octagon sectional shape 62C of the illumination light formed by the light shielding means, and sets σ to be equal in four directions of 0° (vertical to the sheet), 45°, 90°, and 135°.

Again, as the area of the aperture is larger in this case than that of the first embodiment, the light utilization efficiency is improved.

While the third embodiment adopts a regular octagon sectional shape 62C of the illumination light, it may be well to deform the regular octagon, to the extent of the permissible a anisotropy and to reduce a light shielding part by the light shielding means 100 for the improved optical utilization efficiency.

FIG. 3(A) shows a fourth embodiment. The fourth embodiment uses a regular hexagon section of the optical pipe 6 vertical to the optical axis, while the sectional shape of the illumination light formed by the light shielding means is a circle inscribed in a regular hexagon of the optical pipe 6's plane of exit 6b.

FIG. 3(B) shows a fifth embodiment. Similar to the second embodiment, in employing an optical pipe of a regular hexagon section, the fifth embodiment sets a sectional shape 63B of the illumination light formed by the light shielding means 100 to be slightly larger than a circle inscribed in the optical pipe's square plane of exit for the improved optical utilization efficiency.

FIG. 3(C) shows a sixth embodiment. The sixth embodiment provides the light shielding means 100 to shade vertical angle parts on the optical pipe's regular hexagon plane of exit. Thus, the light shielding means 100 has a dodecagonal aperture area 63C.

Figure 4C:
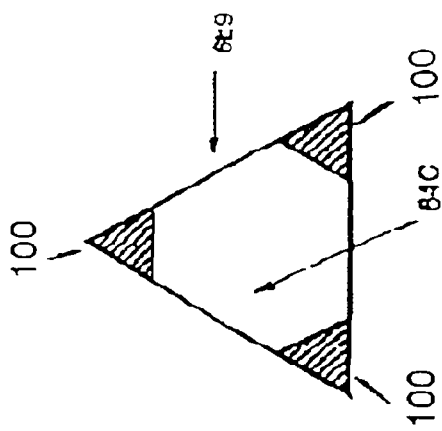
FIG. 4(C) is a view of optical pipe's plane of exit and a light shielding means of a ninth embodiment according to the present invention.
Figure 4B:
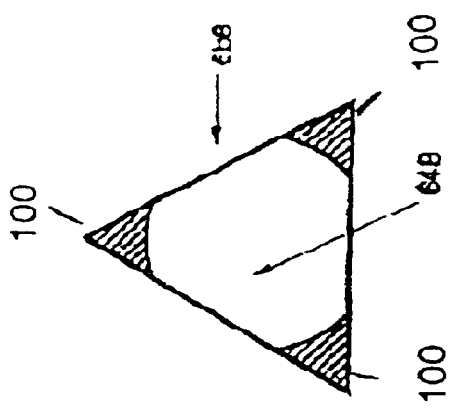
FIG. 4(B) is a view of optical pipe's plane of exit and a light shielding means of an eighth embodiment according to the present invention.
Figure 4A:
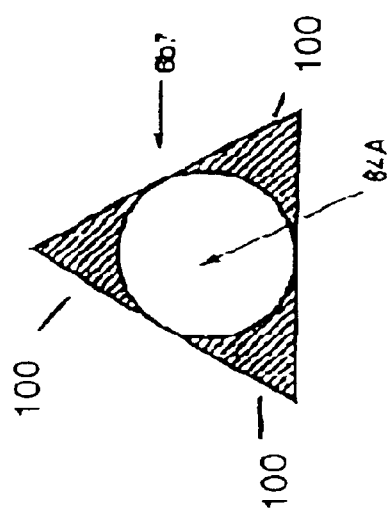
FIG. 4(A) is a view of optical pipe's plane of exit and a light shielding means of a seventh embodiment according to the present invention.

FIG. 4(A) shows a seventh embodiment. The seventh embodiment sets a regular triangle plane of exit for the optical pipe 6, while the illumination light formed by the light shielding means 100 has a circle section 64A inscribed in this regular triangle.

FIG. 4(B) shows an eighth embodiment. In employing an optical pipe having a regular triangle plane of exit, the eighth embodiment sets an aperture part 64B of the light shielding means 100 to be slightly larger than a circle inscribed in this regular triangle for the improved optical utilization efficiency.

FIG. 4(C) shows a ninth embodiment. The ninth embodiment adapts the light shielding means 100 to shade the vertical angle parts on the optical pipe 6's regular triangle plane of exit. Thus, the light shielding means 100 has a hexagonal aperture part 63C.

Figure 7A:
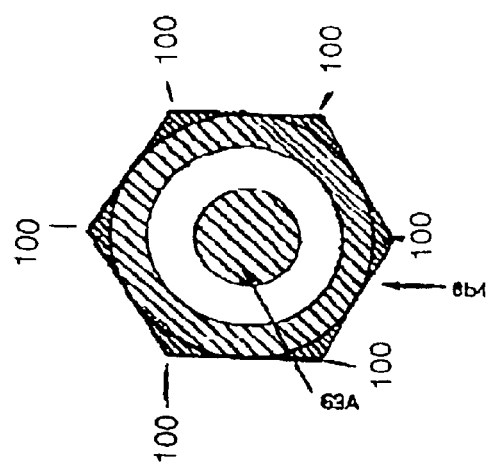
FIG. 7(A) is a view of a light shielding means of a tenth embodiment according to the present invention.

FIG. 7(A) shows a tenth embodiment. The first to ninth embodiments have an object to eliminate the σ anisotropy, whereas this embodiment aggressively uses the light shielding means 100 to deal with a modified illumination mode in the projection exposure apparatus. Thus, this embodiment provides the light shielding means 100 having a ring-belt aperture near the optical pipe 6's plane of exit, and performs a ring-belt illumination for the reticle 10. σ is isotropic when this light shielding means 100 is used.

Figure 7B:
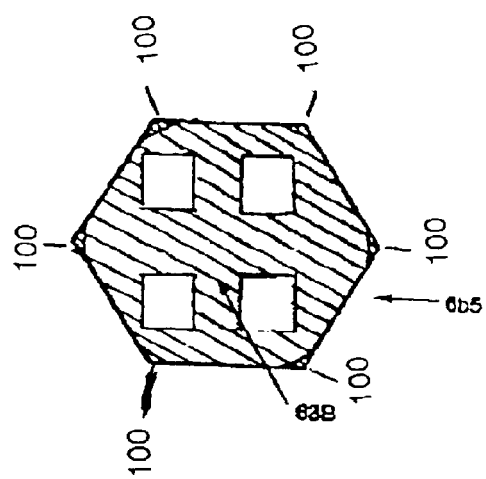
FIG. 7(B) is a view of a light shielding means of an eleventh embodiment according to the present invention.

FIG. 7(B) shows an eleventh embodiment. The first to ninth embodiments have an object to eliminate the σ anisotropy, whereas this embodiment aggressively uses the light shielding means 100 to deal with a modified illumination mode in the projection exposure apparatus. Thus, this embodiment provides a light shielding means 100 having four apertures near the optical pipe 6's plane of exit, and performs a fourfold-pole illumination for the reticle 10.

A description will now be given of an exemplary semiconductor device fabrication method utilizing the above projection exposure apparatus.

Figure 8:
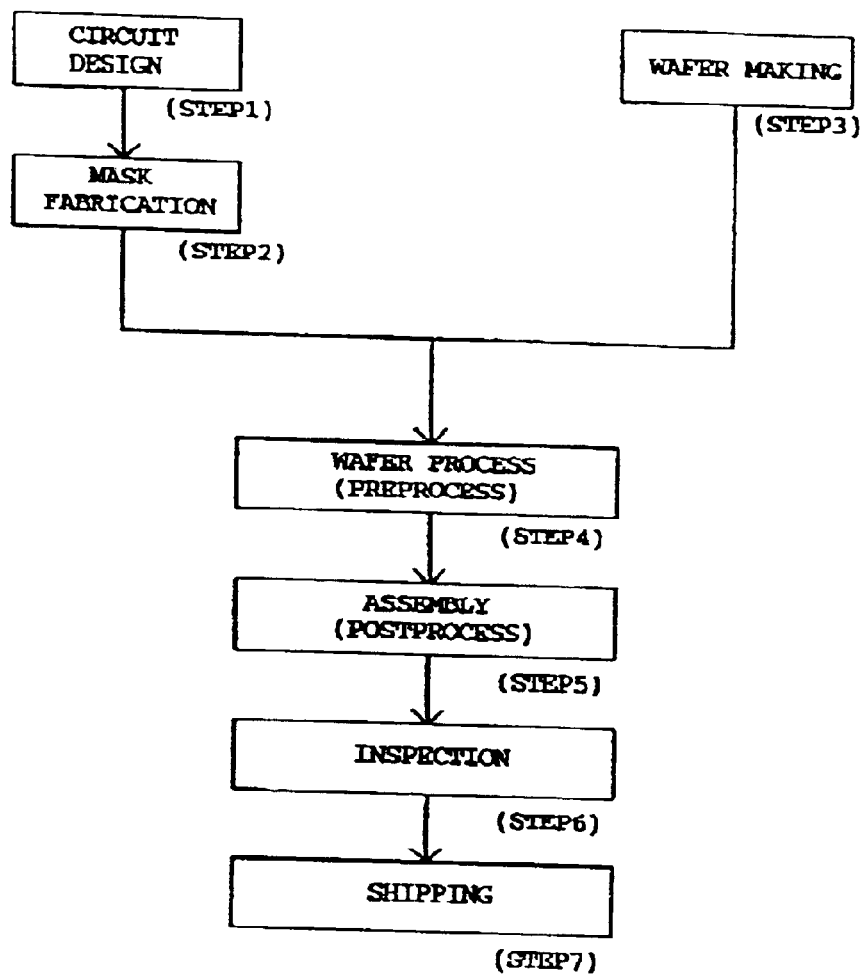
FIG. 8 is a flowchart of a device fabrication method according to the present invention.

FIG. 8 is a flowchart for explaining how to fabricate semiconductor devices (semiconductor chips such as ICs and LSI, liquid crystal panels, CCDs, and the like). Step 1 (circuit design) designs a semiconductor device circuit. Step 2 (mask fabrication) forms a mask having a designed circuit pattern. On the other hand, Step 3 (wafer making) manufactures a wafer using materials such as silicon. Step 4 (wafer process), which is referred to as a pretreatment, forms actual circuitry on the wafer through lithography using the mask and wafer as prepared above. Next, Step 5 (assembly), which is referred to as a posttreatment, forms into a semiconductor chip the wafer formed in Step 4 and includes an assembly step (e.g., dicing, bonding), a packaging step (chip sealing) and the like. Step 6 (inspection) performs various tests for the semiconductor device made in Step 5, such as a validity test and a durability test. Through these steps, a semiconductor device is finished and shipped (Step 7).

Figure 9:
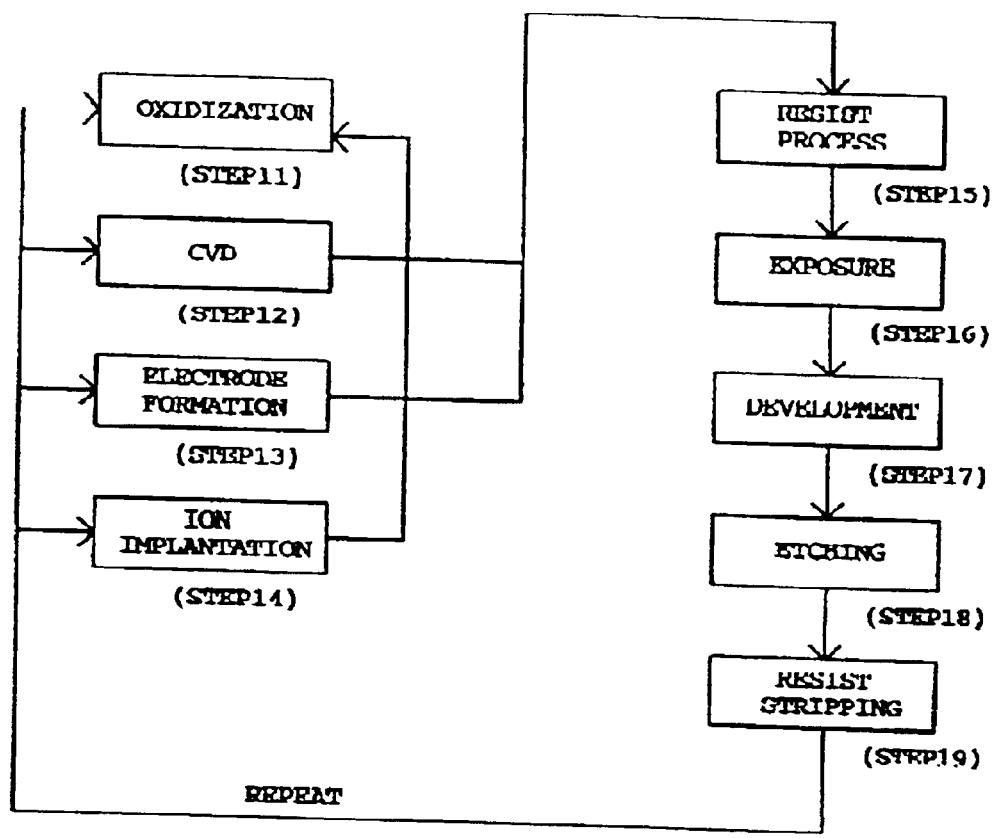
FIG. 9 is a flowchart for a wafer process shown in FIG. 8.

FIG. 9 is a detailed flowchart of the wafer process in Step 4 of FIG. 8. Step 11 (oxidation) oxidizes a wafer's surface. Step 12 (CVD) forms an insulating film on the wafer's surface. Step 13 (electrode formation) forms electrodes on the wafer by vapor disposition and the like. Step 14 (ion implantation) implants ion into the wafer. Step 15 (resist process) applies a photosensitive material onto the wafer. Step 16 (exposure) uses the exposure apparatus described above to expose a circuit pattern on the mask onto the wafer. Step 17 (development) develops the exposed wafer. Step 18 (etching) etches parts other than the developed resist image. Step 19 (resist stripping) removes disused resist after etching. These steps are repeated, and multi-layer circuit patterns are formed on the wafer.

Use of the fabrication method of the instant embodiment will make it possible to fabricate highly integrated semiconductor devices that have conventionally been difficult to fabricate.

Due to a shape of optical pipe's plane of exit, these aforementioned embodiments may supply, despite the σ anisotropy of the projection exposure system, a high quality projection exposure performance to an exposure apparatus which includes an illumination system having an image-forming system which arranges a plane of exit of the beam mixing means (e.g., optical pipe) in an approximately conjugate relationship with a plane of incidence of an optical integrator (e.g., a fly-eye's lens) as multi-beam generating means. In particular, as the above image-forming system as a zoom optical system may make σ variable without lowering the luminous intensities on the reticle and wafer, and without providing a switching mechanism for a σ adjustment stop on the plane of exit of the fly-eye lens, thus realizing a compact illumination system as well as an improved durability. Further, this may not only eliminate the a anisotropy, but also easily provide a desired modified illumination.

What is claimed is:

1. An illumination apparatus comprising:
   an inner-surface reflecting type integrator;
   an optical system for directing a beam from a light source to a portion of incidence of said inner-surface reflecting type integrator;
   an wave-front splitting type integrator;
   an image-forming optical system for arranging a portion of exit of said inner-surface reflecting type integrator approximately conjugate with a portion of incidence of said wave-front splitting type integrator, and for directing a beam from said inner-surface reflecting type integrator to said wave-front splitting type integrator; and
   an irradiating optical system for superimposing multiple beams from said wave-front splitting type integrator on a plane to be irradiated,
   wherein a stop is provided at or near the portion of exit of said inner-surface reflecting type integrator.

2. An illumination apparatus according to claim 1, wherein said inner-surface reflecting optical integrator reflects at least a part of incident light with an internal surface of said inner-surface reflecting optical integrator, and for forming a surface light source on or near the plane of exit of said inner-surface reflecting optical integrator.

3. An illumination apparatus according to claim 1, wherein said wave-front splitting type integrator is a lens array for splitting a wave front of incident light, and for forming multiple secondary light sources on or near the portion of exit of said wave-front splitting type integrator.

4. An illumination apparatus according to claim 1, wherein said stop is a mechanical aperture stop.

5. An illumination apparatus according to claim 1, wherein said stop is made of a light shielding material applied onto the portion of exit of said inner-surface reflecting type integrator.

6. An illumination apparatus according to claim 1, wherein said stop is made of a multi-layer film vapor-deposited onto the portion of exit of said inner-surface reflecting type integrator.

7. An illumination apparatus according to claim 1, wherein said stop is made of a metallic film vapor-deposited onto the portion of exit of said inner-surface reflecting type integrator.

8. An illumination apparatus according to claim 1, wherein said image-forming system is a zoom optical system.

9. An illumination apparatus according to claim 1, wherein the portion of exit of said inner-surface reflecting type integrator has a polygonal shape, and said stop has an aperture for correcting σ anisotropy.

10. An illumination apparatus according to claim 9, wherein said stop has an approximately circular aperture.

11. An illumination apparatus comprising;
    an inner-surface reflecting type integrator including a portion of exit with an n-gonal shape where n is a natural number;
    a wave-front splitting type integrator;
    a zoom optical system for arranging a portion of exit of said inner-surface reflecting type integrator approximately conjugate with a portion of incidence of said wave-front splitting type integrator, and for projecting an image of the portion of exit of said inner-surface reflecting type integrator onto the portion of incidence of said wave-front splitting integrator; and
    an irradiating optical system for superimposing multiple beams from said wave-front splitting integrator on a plane to be irradiated,
    wherein a stop having an approximately circular aperture is provided at or near the portion of exit of said inner-surface reflecting type integrator.

12. A projection exposure apparatus comprising:
    an illumination apparatus for illuminating a mask located on a plane to be illuminated; and
    a projection optical system for projecting a pattern on said mask onto a wafer,
    wherein said illumination apparatus comprising:
    an inner-surface reflecting type integrator;
    an optical system for directing a beam from a light source to a portion of incidence of said inner-surface reflecting type integrator;
    a wave-front splitting type integrator;
    an image-forming optical system for arranging a portion of exit of said inner-surface reflecting type integrator approximately conjugate with a portion of incidence of said wave-front splitting type integrator, and for directing a beam from said inner-surface reflecting type integrator to said wave-front splitting type integrator; and
    an irradiating optical system for superimposing multiple beams from said wave-front splitting type integrator on a plane to be irradiated,
    wherein a stop is provided at or near the portion of exit of said inner-surface reflecting type integrator.

13. A projection exposure apparatus comprising:
    an illumination apparatus for illuminating a mask located on a portion to be illuminated; and
    a projection optical system for projecting a pattern on said mask onto a wafer,
    wherein said illumination apparatus comprising:

an inner-surface reflecting type integrator including a portion of exit with an n-gonal shape where n is a natural number;

a wave-front splitting type integrator;

a zoom optical system for arranging a portion of exit of said inner-surface reflecting type integrator approximately conjugate with a portion of incidence of said wave-front splitting type integrator, and for projecting an image of the portion of exit of said inner-surface reflecting type integrator onto the portion of incidence of said wave-front splitting integrator; and an irradiating optical system for superimposing multiple beams from said wave-front splitting integrator on a plane to be irradiated, wherein a stop having an approximately circular aperture is provided at or near the portion of exit of said inner-surface reflecting type integrator.

14. A device fabrication method comprising the steps of:

projecting a pattern on a mask onto a wafer by using a projection exposure apparatus; and developing said wafer to which said pattern was transferred, wherein said projection exposure apparatus comprising:

an illumination apparatus for illuminating a mask located on a plane to be illuminated; and a projection optical system for projecting a pattern on said mask onto a wafer, wherein said illumination apparatus comprising:

an inner-surface reflecting type integrator;

an optical system for directing a beam from a light source to the portion of exit of said inner-surface reflecting type integrator;

an wave-front splitting type integrator, an image-forming optical system for arranging the portion of incidence of said inner-surface reflecting type integrator approximately conjugate with a portion of incidence of said wave-front splitting type integrator, and for directing a beam from said inner-surface reflecting type integrator to said wave-front splitting type integrator, and an irradiating optical system for superimposing multiple beams from said wave-front splitting type integrator on a plane to be irradiated, wherein a stop is provided at or near the portion of exit of said inner-surface reflecting type integrator.

15. A device fabrication method comprising the steps of:

projecting a pattern on a mask onto a wafer by using a projection exposure apparatus; and developing said wafer to which said pattern was transferred, wherein said projection exposure apparatus comprising:

an illumination apparatus for illuminating a mask located on a plane to be illuminated; and a projection optical system for projecting a pattern on said mask onto a wafer, wherein said illumination apparatus comprising:

an inner-surface reflecting type integrator including a portion of exit with an n-gonal shape where n is a natural number;

a wave-front splitting type integrator;

a zoom optical system for arranging a portion of exit of said inner-surface reflecting type integrator approximately conjugate with a portion of incidence of said wave-front splitting type integrator, and for projecting an image of the portion of exit of said inner-surface reflecting type integrator onto the portion of incidence of said wave-front splitting integrator; and an irradiating optical system for superimposing multiple beams from said wave-front splitting integrator on a plane to be irradiated, wherein a stop having an approximately circular aperture is provided at or near the portion of exit of said inner-surface reflecting type integrator.

* * * * *